US012797175B2

(12) United States Patent
Pan et al.

(10) Patent No.: US 12,797,175 B2
(45) Date of Patent: Nov. 17, 2026

(54) LIVESTOCK AND POULTRY BODY TEMPERATURE MONITORING SYSTEM AND METHOD USING WEARABLE SENSOR AND INFRARED CAMERA

(71) Applicant: ZHEJIANG UNIVERSITY, Zhejiang (CN)

(72) Inventors: Jinming Pan, Zhejiang (CN); Shouyi Wang, Zhejiang (CN); Pengguang He, Zhejiang (CN); Hongjian Lin, Zhejiang (CN); Di Cui, Zhejiang (CN); Yingchun Fu, Zhejiang (CN); Yibin Ying, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 301 days.

(21) Appl. No.: 18/708,600

(22) PCT Filed: Jun. 14, 2023

(86) PCT No.: PCT/CN2023/100248
§ 371 (c)(1),
(2) Date: May 9, 2024

(87) PCT Pub. No.: WO2024/001791
PCT Pub. Date: Jan. 4, 2024

(65) Prior Publication Data

US 2026/0114974 A1 Apr. 30, 2026

(30) Foreign Application Priority Data

Jul. 1, 2022 (CN) ........................ 202210774043.X

(51) Int. Cl.
*A61D 13/00* (2006.01)
*A61B 5/00* (2006.01)
*A61B 5/01* (2006.01)

(52) U.S. Cl.
CPC ............ *A61D 13/00* (2013.01); *A61B 5/0008* (2013.01); *A61B 5/0022* (2013.01);
(Continued)

(58) Field of Classification Search
CPC .... A61D 13/00; A61B 5/0008; A61B 5/0022; A61B 5/0064; A61B 5/015; A61B 2503/40
See application file for complete search history.

(56) References Cited

U.S. PATENT DOCUMENTS

2010/0198024 A1* 8/2010 Elazari-Volcani ..... G16H 10/60 128/903
2015/0282457 A1* 10/2015 Yarden ................ A61D 17/002 340/573.2
(Continued)

FOREIGN PATENT DOCUMENTS

CN 106974625 7/2017
CN 110612921 A * 12/2019 ........... A01K 29/005
(Continued)

OTHER PUBLICATIONS

"Written Opinion of the International Searching Authority (Form PCT/ISA/237) of PCT/CN2023/100248," mailed on Sep. 14, 2023, pp. 1-4.
(Continued)

*Primary Examiner* — Pascal M Bui Pho
*Assistant Examiner* — Nicholas A Robinson
(74) *Attorney, Agent, or Firm* — JCIPRNET

(57) ABSTRACT

The invention discloses a livestock and poultry body temperature monitoring system and method in which a wearable sensor and an infrared camera cooperate. Different breeding region blocks are disposed in a three-dimensional space of a livestock and poultry house, wherein each of the breeding region blocks has a plurality of livestock and poultry individuals, all of the plurality of livestock and poultry individuals in each of the breeding region blocks randomly wear the wearable temperature sensors in a fixed proportion to form sentinel livestock and poultry individuals, the infrared camera obtains group infrared image in an unit of the breeding region blocks, the communication terminal is disposed in the livestock and poultry house, the wearable temperature sensors and the infrared camera are in communication connection with the local server through the communication terminal and the local server is in communication connection with the client through the cloud server.

6 Claims, 4 Drawing Sheets

(52) U.S. Cl.
CPC ............ *A61B 5/0064* (2013.01); *A61B 5/015* (2013.01); *A61B 2503/40* (2013.01)

(56) References Cited

U.S. PATENT DOCUMENTS

| | | | | |
|---|---|---|---|---|
| 2017/0156288 A1* | 6/2017 | Singh | .................... | A01K 11/002 |
| 2018/0295809 A1* | 10/2018 | Yajima | .................. | A01K 11/008 |
| 2019/0130728 A1* | 5/2019 | Struhsaker | ........... | A01K 29/005 |
| 2023/0019190 A1* | 1/2023 | Shamsuddin | ............. | G06T 7/20 |
| 2023/0342902 A1* | 10/2023 | Manafiazar | ........... | G06T 7/0002 |

FOREIGN PATENT DOCUMENTS

| | | |
|---|---|---|
| CN | 111626985 | 9/2020 |
| CN | 112945395 | 6/2021 |
| CN | 114980011 | 8/2022 |
| JP | 2018074910 | 5/2018 |

OTHER PUBLICATIONS

"International Search Report (Form PCT/ISA/210) of PCT/CN2023/100248," mailed on Sep. 14, 2023, with English translation thereof, pp. 1-6.

* cited by examiner

LIVESTOCK AND POULTRY BODY TEMPERATURE MONITORING SYSTEM AND METHOD USING WEARABLE SENSOR AND INFRARED CAMERA

CROSS-REFERENCE TO RELATED APPLICATION

This application is a 371 of international application of PCT application serial no. PCT/CN2023/100248, filed on Jun. 14, 2023, which claims the priority benefit of China application no. 202210774043.X, filed on Jul. 1, 2022. The entirety of each of the above-mentioned patent applications is hereby incorporated by reference herein and made a part of this specification.

TECHNICAL FIELD

The present invention relates to a field of body temperature monitoring of livestock and poultry, in particular to multisource body temperature monitoring based on combination of wearable temperature sensor's sentinel individual continuous monitoring and infrared camera's wide-area flexible patrol inspection and a monitoring system and method for evaluating livestock and poultry body temperature health conditions and carrying out abnormal early warning.

DESCRIPTION OF RELATED ART

Livestock and poultry are endothermic animals. As an important indicator of the physiological functions of livestock and poultry, body temperature can reflect the health status of livestock and poultry to a great extent. The abnormal state of an individual can be sensed and found earlier and action can be taken in time in the actual breeding production process, and the production loss can be reduced.

Traditional breeding farms often use manual random patrol inspection to monitor the body temperature of livestock and poultry individuals, measuring the anal temperature to characterize the core body temperature of livestock and poultry. This is labor-intensive and can easily cause stress reactions in livestock and poultry, and cannot achieve continuous monitoring. Currently, there are some body temperature monitoring manners based on temperature sensors and infrared cameras, these methods can better detect the body temperature of individuals, but only use a single threshold method for monitoring based on temperature data, this method is relatively rough and ignores the changes in body temperature caused by the growth stage and work rest cycle. It does not consider the temporal characteristics of body temperature changes. It has problems such as single bias results and poor robustness, which is not ideal to the precision requirements of breeding. (For example, for animals with high body temperatures during the day, the daytime temperature maintained at night is actually abnormal, but a single threshold method cannot be classified in this dimension). In addition, in the context of unmanned large-scale breeding, the use of a single temperature sensor monitoring manner has problems such as falling off and malfunctioning that affect data stability. The cost of using an infrared camera to monitor a single application is high, and the patrol inspection method cannot achieve continuous monitoring for obtaining better timing characteristics.

SUMMARY

In order to solve the problems existing in the background technology, the purpose of the present invention is to provide a livestock and poultry body temperature monitoring system and method that coordinates wearable temperature sensor monitoring and infrared camera patrol inspection, by integrating the data from continuous high-precision monitoring of sentinel individual wearable temperature sensor with multi-source temperature data from the infrared camera's wide-area flexible patrol inspection, and introducing timing features to build a body temperature change model, it can realize livestock and poultry body temperature monitoring, health status feedback and abnormal early warning.

The technical solutions adopted by the present invention to solve the technical problems are:

1. A livestock and poultry body temperature monitoring system in which a wearable sensor and an infrared camera cooperate:

A plurality of wearable temperature sensors, an infrared camera, a communication terminal, a local server, a cloud server and a client are included;

Different breeding region blocks are disposed within a three-dimensional space of a livestock and poultry house, wherein each of the breeding region blocks has a plurality of livestock and poultry individuals, all of the plurality of livestock and poultry individuals in each of the breeding region blocks randomly wear the wearable temperature sensors in a fixed proportion to form sentinel livestock and poultry individuals, the infrared camera obtains group infrared image in an unit of the breeding region blocks, the communication terminal is disposed in the livestock and poultry house, the wearable temperature sensors and the infrared camera are in communication connection with the local server through the communication terminal and the local server is in communication connection with the client through the cloud server.

The infrared camera performs patrol inspection between the breeding region blocks in the livestock and poultry house along a preset infrared camera patrol inspection route.

The livestock and poultry house is divided into a specific number of breeding region blocks and numbered according to the three-dimensional space structure. Individuals in the breeding region block are randomly selected as sentinels according to a specific proportion, and wearable temperature sensors are worn to monitor the body temperature and health state of the groups in the region.

The wearable temperature sensor has a battery voltage collecting circuit and a wireless communication module for battery replacement notification. The collected data is transmitted to the communication terminal through the wireless data transmission protocol.

2. A livestock and poultry body temperature monitoring method in which a wearable sensor and an infrared camera cooperate. The method includes the following steps:

S1: Data Obtaining

Continuous body temperature data of an appropriate number of the sentinel livestock and poultry individuals in the breeding region blocks are obtained through the wearable temperature sensors, and location of the breeding area blocks and infrared thermal images of all of the livestock and poultry individuals in each of the breeding area blocks are collected through patrol inspection of the infrared cameras;

S2: data transmission and preprocessing

The communication terminal transmits the continuous body temperature data and infrared thermal imaging data collected in step S1 to the local server, the local server respectively performs screening and image segmentation preprocessing on the data to obtain a body temperature value, and the body temperature value after preprocessed is used for processing to obtain a body temperature monitoring curve of each of the livestock and poultry individuals changing over time.

The communication terminal transmits the continuous body temperature data and infrared thermal imaging data collected in step S1 to the local server. The local server performs screening and preprocessing of image segmentation on the data to obtain the body temperature value. The body temperature value after preprocessing is processed to obtain each The body temperature monitoring curve of a livestock and poultry individual changes over time;

S3: Database Building and Model Training

A growth stage-temperature database is built by using the body temperature monitoring curve changing over time which is obtained in step S2 under different breeds, different growth stages and different monitoring manners, and a normal body temperature change zone (model of body temperature changing over time) is obtained through processing the growth stage-temperature database;

S4: State Determination and Data Review

Whether the temperature state is abnormal or not is determined by using timing match and outlier identification to the temperature values collected in real time combining with the normal temperature change zone, and the breeding region blocks where the livestock and poultry with the abnormal temperature state are located is determined as an abnormal region, and the infrared camera is moved to the abnormal area for rechecking to realize complete monitoring.

The Step S2 is:

The continuous temperature data collected by the wearable temperature sensors is compared with a fluctuation range threshold to determine an abnormal value, the abnormal value appearing as an individual is removed but the abnormal value appearing continuously is retained, and each of the temperature values that is obtained is retained as the body temperature values of the livestock and poultry individuals;

For the infrared thermal image collected by the infrared camera, instance segmentation on the infrared thermal image of each of the breeding region blocks is performed by using a deep learning method to identify each of the livestock and poultry individuals, each of the livestock and poultry individuals in the breeding region blocks is renumbered, and key pixel points and temperature information thereof in the image where each of the livestock and poultry individuals is located is retrieved as the body temperature values of the livestock and poultry individuals;

The body temperature values $T_s$ and $T_c$ directly monitored by the wearable temperature sensors and the infrared camera are respectively processed according to the following formula to obtain core body temperature values $T_{sc}$ and $T_{cc}$, the formula is as follows:

$$T_{sc} = a_s T_s + b_s$$

$$T_{cc} = a_c T_c + b_c$$

wherein $a_s$, $b_s$ are respectively a weight and a correction constant of the wearable temperature sensors, $a_c$, $b_c$ are respectively the weight and a correction constant of the infrared camera.

Step S3 is: under conditions of different breeds, different growth stages and different monitoring manners, collecting the body temperature values through the wearable temperature sensors and the infrared camera, and building the normal body temperature change zone at different growth stages under the same breeds and various monitoring manners.

During monitoring, the body temperatures of the corresponding timing are simultaneously established using machine learning methods, which is different from the single threshold setting method to build a normal body temperature change zone.

The monitoring method refers to the position where the wearable temperature sensor is worn.

In step S3, there are two steps for abnormality determination:

Step 1: comparing the temperature value collected in real time with the normal body temperature change zone, and determining whether the temperature value falls into the normal body temperature change zone:

if not, a body temperature state of a livestock and poultry corresponding to the temperature value is abnormal, and step 2 is performed;

if so, the body temperature state of the livestock and poultry corresponding to the temperature value is not abnormal, and step 3 is performed;

Step 2: comparing the temperature value with a range [μ−3σ, μ+3σ] determined by the following formula:

$$\mu = \frac{\sum_{i=1}^{n} T_{cci}}{n}$$

$$\sigma = \sqrt{\frac{\sum_{i=1}^{n} (T_{cci} - \mu)^2}{n-1}}$$

Wherein μ is an average value of a group temperature, σ is a standard deviation of the group temperature, $T_{cci}$ is the body temperature values of the group monitored by the wearable temperature sensors and the infrared camera, and n is the number of the group;

the group is divided into two conditions of all of the livestock and poultry individuals in a single breeding region block and all of the livestock and poultry individuals in all of the breeding region blocks, comparison and determining are respectively performed between the temperature values of the livestock and poultry individuals and the group formed by all of the livestock and poultry individuals in the single breeding region block, and between the temperature values of the livestock and poultry individuals and the group formed by all of the livestock and poultry individuals in all of the breeding region blocks:

if the temperature value is within the range [μ−3σ, μ+3σ], the body temperature state of the livestock and poultry corresponding to the temperature value is not abnormal;

if the temperature value is not within the range [μ−3σ, μ+3σ], the body temperature state of the livestock and poultry corresponding to the temperature value is abnormal;

Step 3: selecting the livestock and poultry with abnormal body temperature state, moving the infrared camera to the breeding region block (4) where the livestock and poultry with the abnormal body temperature state are located, rechecking the livestock and poultry, and further monitoring the abnormal condition.

Compared with existing inventions, the beneficial effects of the present invention are:

1. This method and system uses two methods to monitor and evaluate the temperature status of individuals and groups in livestock and poultry houses, preprocessing temperature data collected from multiple sources, and can stably characterize and monitor their core temperature;
2. This method optimizes the method of body temperature monitoring and abnormality determination, introduces timing features, and build a model of body temperature changing over time based on breed-growth stage-monitoring method, distinguishes a single threshold determination method, and more accurately identifies abnormal individuals;
3. This method optimizes the body temperature monitoring and abnormality determination methods, and proposes an outlier abnormality determination method based on big data, which can effectively identify possible abnormal individuals;
4. The method and system adopt breeding region blocks and sentinel individual solutions to evaluate individual and group state by monitoring the sentinel state. The division of breeding region block facilitates data analysis, processing and rapid locating;
5. Through this method and system, the collaborative multi-source data collection of wearable sensors and infrared cameras greatly reduces the possibility of system misjudgment and can obtain more stable and accurate body temperature data;
6. Real-time body temperature monitoring can provide timely understanding of livestock and poultry abnormalities and early prevention to avoid large-scale losses.

DESCRIPTION OF THE EMBODIMENTS

The following detailed description of embodiments of the present invention is provided in connection with the accompanying drawings and examples. The following examples are intended to illustrate the invention but are not intended to limit the scope of the invention.

Figure 1:
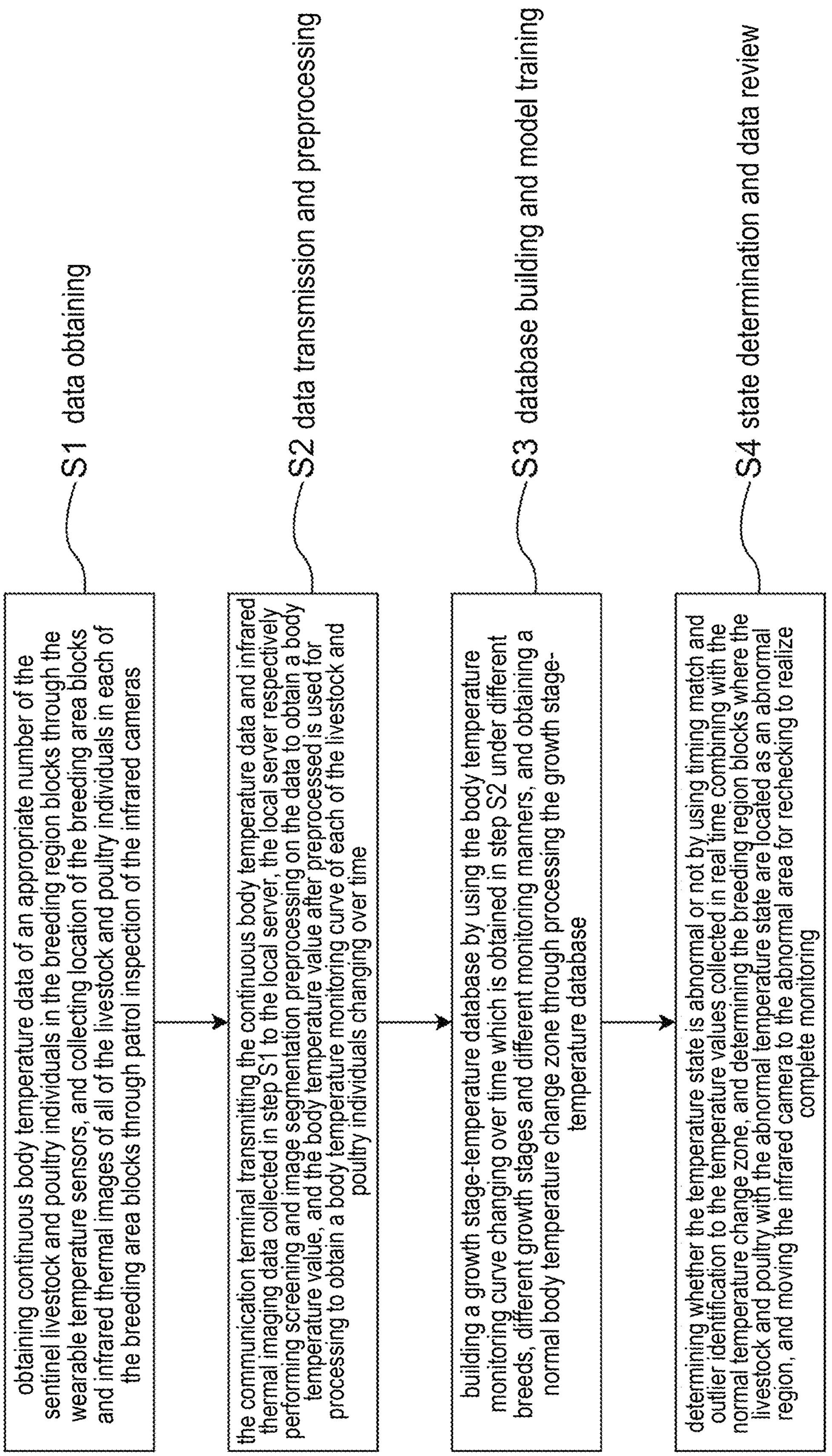
FIG. 1 is a process flow according to an embodiment of the present invention.
Figure 2:
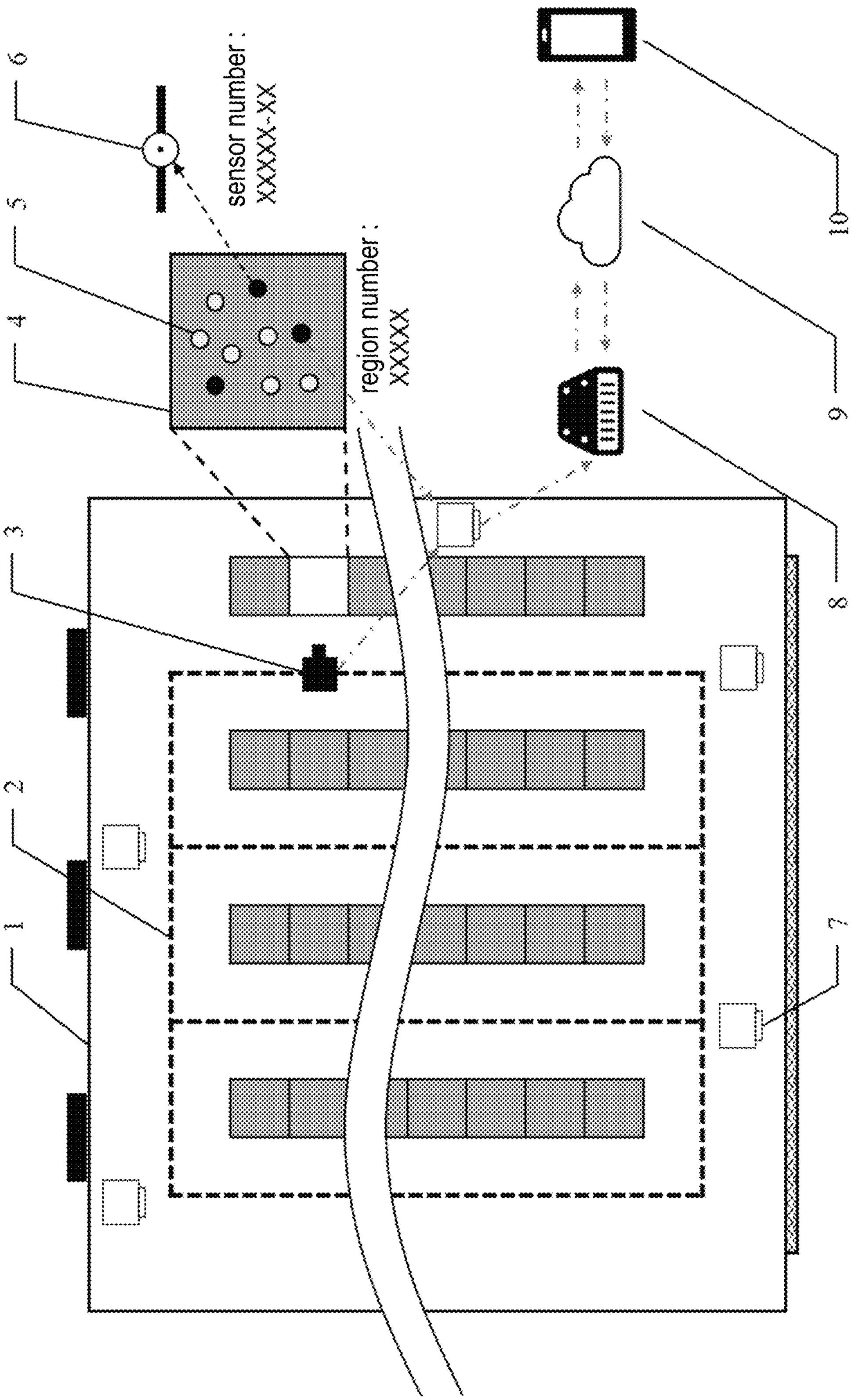
FIG. 2 is a schematic structural view of the system according to the embodiment of the present invention.
Figure 3:
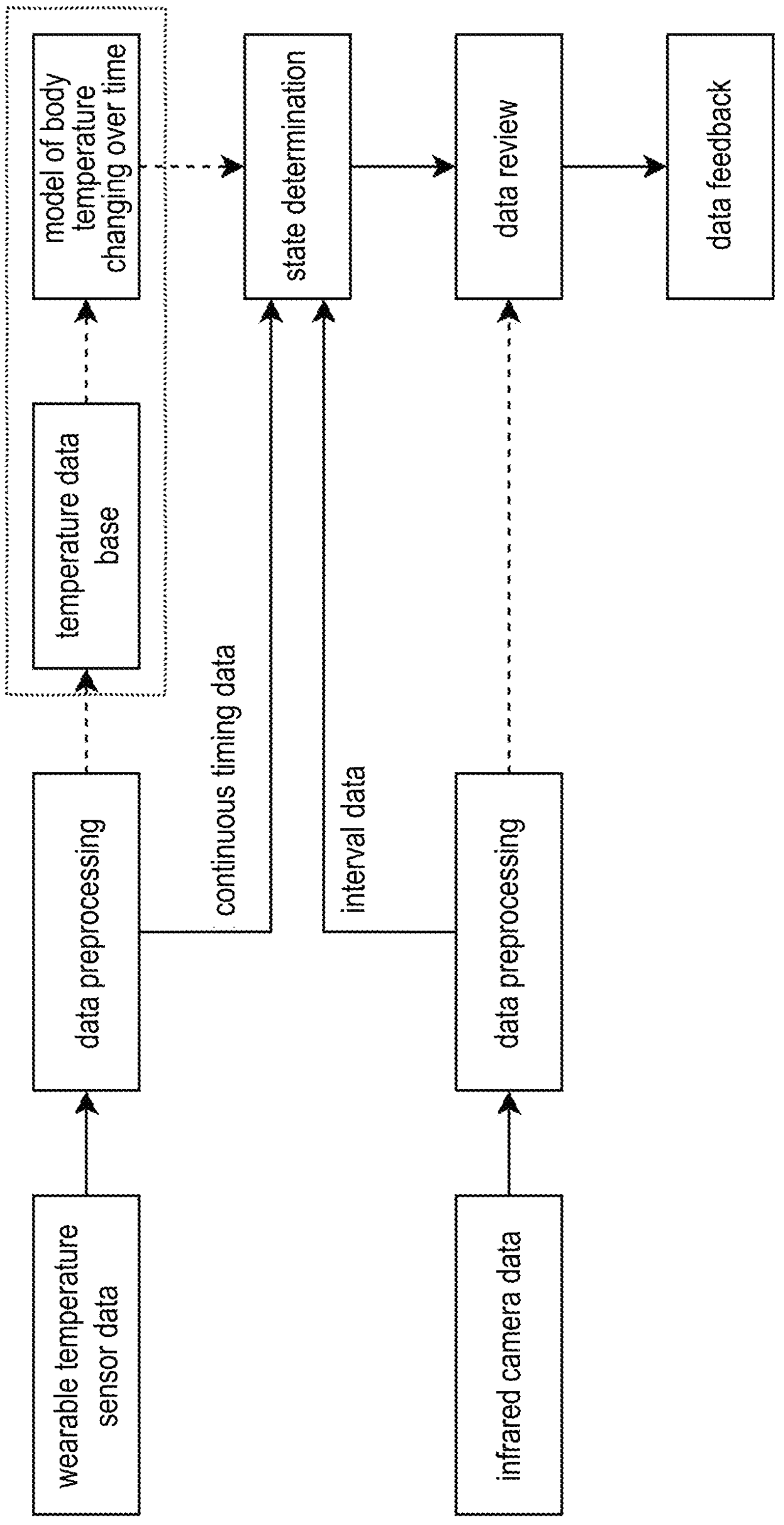
FIG. 3 is a schematic diagram of the comprehensive body temperature assessment workflow according to the embodiment of the present invention.

As shown in FIG. 2, the system includes a plurality of wearable temperature sensors 6, an infrared camera 3, a communication terminal 7, a local server 8, a cloud server 9 and a client 10;

A livestock and poultry house is configured with different breeding region blocks 4 within its own three-dimensional space, wherein each of the breeding region blocks 4 has a plurality of livestock and poultry individuals 5, all of the plurality of livestock and poultry individuals in each of the breeding region blocks 4 randomly wear the wearable temperature sensors 6 in a fixed proportion to form sentinel livestock and poultry individuals, the infrared camera 3 obtains group infrared image in an unit of the breeding region blocks, the communication terminal 7 is disposed in the livestock and poultry house 1, the wearable temperature sensors (6) and the infrared camera 3 are in communication connection with the local server (8) through the communication terminal 7 and the local server 8 is in communication connection with the client 10 through the cloud server 9.

The infrared camera 3 performs patrol inspection between the breeding region blocks 4 in the livestock and poultry house 1 along a preset infrared camera patrol inspection route 2.

The data collected by the wearable temperature sensors 6 and the infrared camera 3 are uploaded to the local server 8. The local server 8 or cloud server 9 performs preprocessing on the data and then enters a normal body temperature change zone to perform state determination of livestock and poultry body temperatures, quickly locates the breeding region block where the livestock and poultry with abnormal body temperature is, and then the infrared camera 3 is configured to photograph and review the breeding region block where the livestock and poultry with abnormal body temperature is to complete the monitoring.

After review, the body temperature health status of individuals and groups can be comprehensively assessed based on temperature data, and the results and warning information are transmitted to the user through client 10.

The livestock and poultry house is divided into a specific number of breeding region blocks according to the three-dimensional space structure. Each of the breeding region blocks corresponds to a specific serial number. The specific number of the livestock and poultry individuals in each of the breeding region blocks is defined as sentinel livestock and poultry individuals, the sentinel livestock and poultry individuals wear wearable temperature sensors to continuously monitor individual body temperature changes, directly and indirectly reflect group state, and provides functions of body temperature monitoring and early warning in the region.

The infrared patrol inspection camera moves in the livestock and poultry house along the preset slide rails or tracks in the livestock and poultry house, and takes at least one thermal image of each of the breeding region blocks to collect the body temperature data of the livestock and poultry. The image information also includes positioning data of the breeding region blocks and timing information.

The wearable temperature sensor 5 has a battery voltage collecting circuit and a wireless communication module for battery replacement notification. The collected data is transmitted to the communication terminal 7 through the wireless data transmission protocol.

The wearable temperature sensor 5 is coin-shaped and adopts a modular design. It can incorporate with customized accessories such as silica gel strap, silica gel earrings and stably wear at a position that can be used to stably characterize the body temperature of the individual, including but not limited to the underwings of chickens, ears of pigs, etc.

The wearable temperature sensors 5 continuously collects data. Sampling frequency can be set according to actual needs. The collected information includes timing characteristics and location information. The data collected by the infrared camera 3 includes regional information and corresponds to the timing characteristics of the data collected by the wearable temperature sensors 5.

The wearable temperature sensor monitors 24 hours a day at a certain sampling frequency, and the sampling data also includes timing characteristics and location information; the wearable temperature sensor is an additional accessory worn on the corresponding livestock and poultry at a position that can be used to stably characterize the body temperature of the individual, including but not limited to the underwings of chickens, ears of pigs, etc.;

Preset the track for the patrol inspection infrared camera in the livestock and poultry house, set patrol inspection program of the patrol inspection infrared camera according to the previously divided regions, stay in the corresponding area during the patrol inspection, and take more than one infrared thermal image that meets the requirements in the region, wherein the shooting angle reduces blocking as possible;

The wearable temperature sensor and infrared camera transmit the collected data to the communication terminal through the wireless data transmission protocol. The data contains timing characteristics and location information. The communication terminal uploads the data to the server at a certain time frequency; the collected data can be processed by a locally deployed server or directly uploaded to the cloud server for processing. It can be flexibly arranged according to the actual situation.

When the system is actually deployed, the local servers and the cloud servers can be flexibly arranged to facilitate localized processing and offline processing, and solutions can be flexibly selected to improve computing efficiency and reduce costs. When the local server 8 has sufficient computing power, the collected data can be processed directly offline. Otherwise, the data can also be processed directly on the cloud server 9.

When the system is actually applied, based on the temperature sensor, the infrared camera and multi-source temperature data, after preprocessing, abnormal individuals are tracked based on two abnormal determination methods, and the infrared camera data is used for verification, and the comprehensive expert system further diagnoses the abnormal objects and feeds them back to user;

The system can continuously optimize the body temperature model based on the collected data during actual application to improve the stability of the system.

The implementation process of the present invention is as follows:

S1: Data Obtaining

The continuous high-precision body temperature data of an appropriate number of sentinel livestock and poultry individuals in the breeding region block 4 are obtained respectively through the wearable temperature sensors 6, and the infrared thermal image and infrared thermal image of all of the livestock and poultry individuals in each of the breeding region block 4 are collected through patrol inspection of the infrared camera 3, so that infrared thermal imaging data and positioning data of more livestock and poultry are covered;

S2: Data Transmission and Preprocessing

The communication terminal 7 respectively transmits the continuous body temperature data and infrared thermal imaging data collected in step S1 to the local server 8. The local server 8 performs screening and preprocessing of image segmentation on the data to obtain the body temperature value. The image segmentation specifically comprises the segmentation of the heads of the livestock and poultry, and the body temperature monitoring curves of each of the livestock and poultry individuals, which change over time, are obtained by processing the preprocessed body temperature values.

S3: Database Building and Model Training

A growth stage-temperature database is built by using the body temperature monitoring curve changing over time which is obtained in step S2 under different breeds, different growth stages and different monitoring manners, and a normal body temperature change zone is obtained through processing the growth stage-temperature database;

S4: State Determination and Data Review

Whether the temperature state is abnormal or not is determined by using timing match and outlier identification to the temperature values collected in real time combining with the normal temperature change zone, and the breeding region blocks 4 where the livestock and poultry with the abnormal temperature state are located is determined as an abnormal region, and the infrared camera 3 is moved to the abnormal area for rechecking to realize complete monitoring.

Finally, the temperature data can be integrated to provide assessment and feedback on the group body temperature and health state of each of the breeding region blocks of the livestock and poultry house.

Step S2 is: comparing the continuous temperature data collected by the wearable temperature sensors with a fluctuation range threshold to determine an abnormal value, removing the abnormal value appearing as an individual but retaining the abnormal value appearing continuously, and retaining each of the temperature values that is obtained as the body temperature values of the livestock and poultry individuals; the retaining of the abnormal values which appear continuously means that the abnormal values appear continuously for more than 5 times or more than 15 min.

For the infrared thermal image collected by the infrared camera, instance segmentation is performed on the infrared thermal image of each of the breeding region blocks by using a deep learning method to identify each of the livestock and poultry individuals, each of the livestock and poultry individuals in the breeding region blocks are renumbered, and key pixel points and temperature information thereof in the image where each of the livestock and poultry individuals is located are retrieved as the body temperature values of the livestock and poultry individuals;

The body temperature values $T_s$ and $T_c$ directly monitored by the wearable temperature sensor and the infrared camera are respectively processed according to the following formula to obtain core body temperature values $T_{sc}$ and $T_{cc}$, the formula is as follows:

$$T_{sc} = a_s T_s + b_s$$

$$T_{cc} = a_c T_c + b_c$$

wherein $a_s$, $b_s$ are respectively a weight and a correction constant of the wearable temperature sensors, $a_c$, be are respectively the weight and a correction constant of the infrared camera. The values of a and b are preset according to the monitored object and the monitoring mode.

Step S3 is: under conditions of different breeds, different growth stages and different monitoring manners, the body temperature values are collected through the wearable temperature sensors 6 and the infrared camera 3, and the normal body temperature change zone is built at different growth stages under the same breeds and various monitoring manners, and the normal body temperature change zone includes an upper curve and a lower curve and serve as a model of body temperature changing over time.

Figure 4:
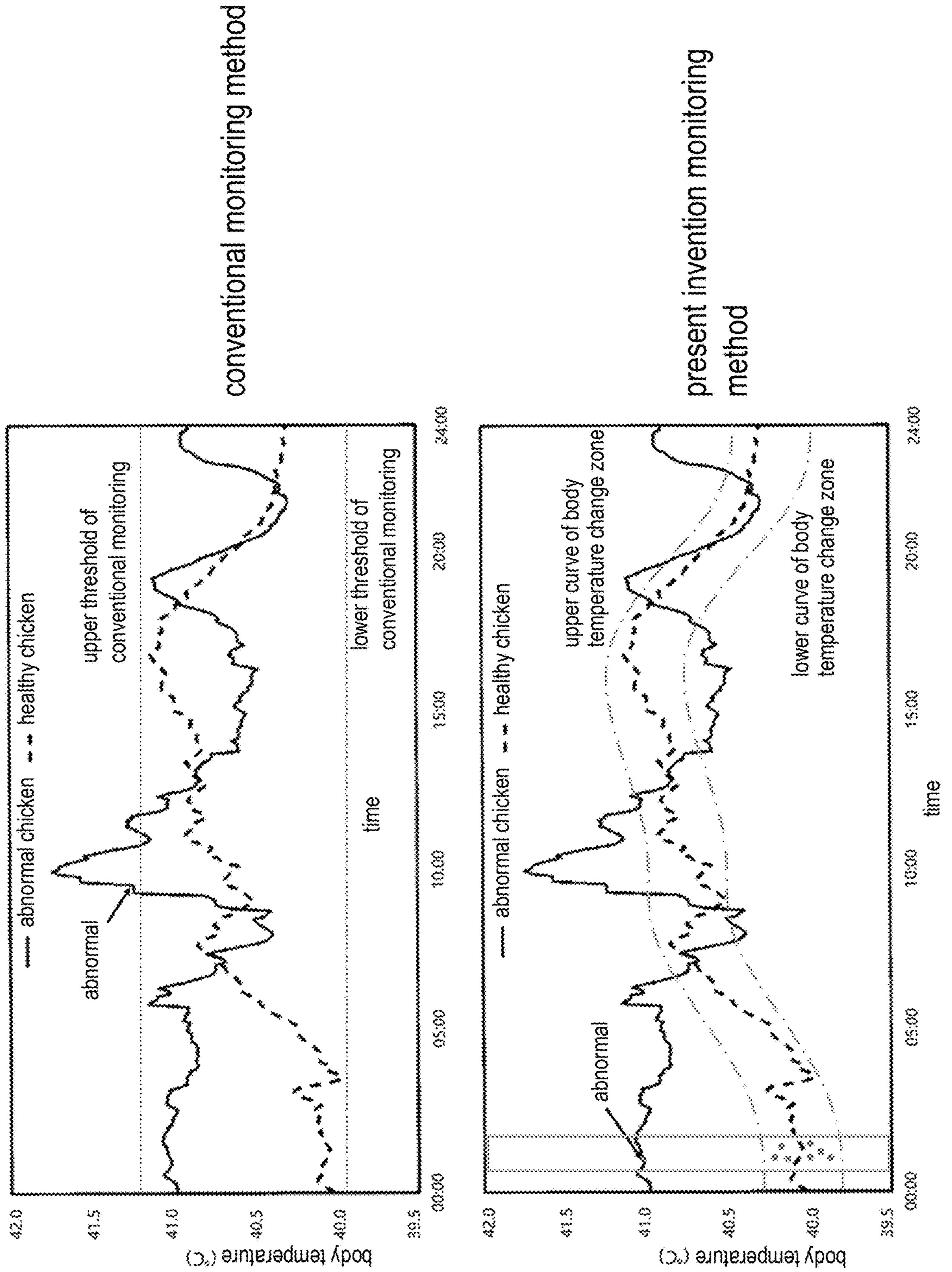
FIG. 4 is a comparison diagram between the embodiment of the present invention and the traditional body temperature monitoring method.

Specifically is:

Step 1: comparing the temperature value collected in real time with the normal body temperature change zone, and determining whether the temperature value falls into the normal body temperature change zone:

if not, a body temperature state of a livestock and poultry corresponding to the temperature value is abnormal, and step 2 is performed;

if so, the body temperature state of the livestock and poultry corresponding to the temperature value is not abnormal, and step 3 is performed;

Step 2: comparing the temperature value with a range [μ−3σ, μ+3σ] determined by the following formula:

$$\mu = \frac{\sum_{i=1}^{n} T_{cci}}{n}$$

$$\sigma = \sqrt{\frac{\sum_{i=1}^{n} (T_{cci} - \mu)^2}{n-1}}$$

Wherein μ is an average value of a group temperature, σ is a standard deviation of the group temperature, $T_{cci}$ is the body temperature values of the group monitored by the wearable temperature sensors and the infrared camera, and n is the number of the group;

The group is divided into two conditions of all of the livestock and poultry individuals in a single breeding region block and all of the livestock and poultry individuals in all of the breeding region blocks, comparison and determining are respectively performed between the temperature values of the livestock and poultry individuals and the group formed by all of the livestock and poultry individuals in the single breeding region block, and between the temperature values of the livestock and poultry individuals and the group formed by all of the livestock and poultry individuals in all of the breeding region blocks according to the range [μ−3σ, μ 3σ].

if the temperature value is within the range [μ−3σ, μ+3σ], the body temperature state of the livestock and poultry corresponding to the temperature value is not abnormal;

if the temperature value is not within the range [μ−3σ, μ+3σ], the body temperature state of the livestock and poultry corresponding to the temperature value is abnormal;

As shown in the embodiment in FIG. 4, compared with the traditional body temperature monitoring method of setting a fixed threshold, this method can determine abnormal individuals at least 10 hours in advance.

Step 3: selecting the livestock and poultry with abnormal body temperature state, moving the infrared camera to the breeding region block 4 where the livestock and poultry with the abnormal body temperature state are located, rechecking the livestock and poultry, and further monitoring the abnormal condition.

It can be seen that the present invention sets up a breeding region block and sentinel livestock and poultry individuals, uses two methods to monitor and evaluate the body temperature state of livestock and poultry individuals and groups, can stably characterize and monitor their core temperature, and helps to quickly positioning and analysis of group status; the method of body temperature monitoring and abnormality determination is optimized, timing features are introduced, and a model of body temperature changing over time of growth stage-temperature is built. At the same time, a big data-based outlier abnormality determination method is proposed, which can effectively lock in possible abnormal individuals; multi-source data collection and infrared camera review can obtain more stable and accurate body temperature data, greatly reducing the possibility of system misjudgment; real-time body temperature monitoring can provide timely understanding of livestock and poultry abnormalities and early prevention to avoid large-scale losses.

What is claimed is:

1. A livestock and poultry body temperature monitoring system in which a wearable sensor and an infrared camera cooperate, comprising:

a plurality of wearable temperature sensors, the infrared camera, a communication terminal, a local server, a cloud server, and a client;

a livestock and poultry house having a three-dimensional space in which a plurality of breeding region blocks are disposed, wherein each of the plurality of breeding region blocks has a plurality of livestock and poultry individuals, wherein, in each of the plurality of breeding region blocks, a fixed proportion of the plurality of livestock and poultry individuals in the respective breeding region block are randomly selected to wear respective wearable temperature sensors of the plurality of wearable temperature sensors to form sentinel livestock and poultry individuals, the infrared camera obtains a group infrared image for each of the plurality of breeding region blocks, the communication terminal is disposed in the livestock and poultry house, the plurality of wearable temperature sensors and the infrared camera are in communication connection with the local server through the communication terminal, and the local server is in communication connection with the client through the cloud server;

wherein the local server is configured to:

receive, from the communication terminal, continuous body temperature data obtained from an appropriate number of the sentinel livestock and poultry individuals in the plurality of breeding region blocks through the plurality of wearable temperature sensors, location data of each of the plurality of breeding region blocks, and infrared thermal imaging data of the plurality of livestock and poultry individuals in each of the plurality of breeding region blocks collected through patrol inspection by the infrared camera;

perform screening on the continuous body temperature data and image segmentation preprocessing on the infrared thermal imaging data to obtain preprocessed body temperature values, and analyze the preprocessed body temperature values to generate a temporal body temperature monitoring curve for each of the plurality of livestock and poultry individuals in each of the plurality of breeding region blocks;

build a growth stage-temperature database based on the temporal body temperature monitoring curves according to different breeds, different growth stages, and different monitoring manners, and process the growth stage-temperature database to obtain a normal body temperature change zone; and determine, based on a timing match and outlier identification applied in real time to the preprocessed body temperature values in combination with the normal body temperature change zone, whether a body temperature state of a livestock and poultry individual is abnormal, designate one of the plurality of breeding region blocks in which the livestock and poultry individual is located as an abnormal region, and cause the infrared camera to move to the abnormal region to recheck the livestock and poultry individual and complete monitoring.

2. The livestock and poultry body temperature monitoring system of claim 1, wherein the infrared camera performs patrol inspection between the plurality of breeding region blocks in the livestock and poultry house along a preset infrared camera patrol inspection route.

3. The livestock and poultry body temperature monitoring system of claim 1, wherein each of the plurality of wearable temperature sensors has a battery, a battery voltage collecting circuit, and wireless communication circuitry configured to transmit a notification to replace the battery and to transmit the continuous body temperature data collected by the respective wearable temperature sensor to the communication terminal through a wireless data transmission protocol.

4. The livestock and poultry body temperature monitoring system of claim 1, wherein the local server is further configured to:

compare the continuous body temperature data collected by each of the plurality of wearable temperature sensors with a fluctuation range threshold to identify an abnormal value in the continuous body temperature data, remove the abnormal value when the abnormal value appears individually, retain the abnormal value when the abnormal value appears continuously, and retain each of resulting temperature value as a body temperature value of a corresponding sentinel livestock and poultry individual;

perform image segmentation preprocessing on the infrared thermal imaging data, wherein the image segmentation preprocessing comprises segmentation of heads of the plurality of livestock and poultry individuals in each of the plurality of breeding region blocks, and retrieve, from the infrared thermal imaging data, temperature information associated with the segmented heads as body temperature values monitored by the infrared camera for the plurality of livestock and poultry individuals in each of the plurality of breeding region blocks; and process a body temperature values $T_s$ directly monitored by one of the plurality of wearable temperature sensors and a body temperature value $T_c$ directly monitored by the infrared camera respectively, according to the following formulas to obtain core body temperature values $T_{sc}$ corresponding to $T_s$ and a core body temperature value $T_{cc}$ corresponding to $T_c$:

$$T_{sc} = a_s T_s + b_s$$

$$T_{cc} = a_c T_c + b_c$$

wherein $T_s$ represents the body temperature value directly monitored by one of the plurality of wearable temperature sensors, $T_c$ represents the body temperature value directly monitored by the infrared camera, $T_{sc}$ represents the core body temperature value corresponding to $T_s$, $T_{cc}$ represents the core body temperature value corresponding to $T_c$, $a_s$ and $b_s$ are respectively a weight and a correction constant of the plurality of wearable temperature sensors, and $a_c$ and $b_c$ are respectively a weight and a correction constant of the infrared camera.

5. The livestock and poultry body temperature monitoring system of claim 4, wherein the local server is further configured to: build respective normal body temperature change zones for the different growth stages of each of the different breeds and for each of the different monitoring manners based on body temperature values collected through the plurality of wearable temperature sensors and the infrared camera under the different breeds, the different growth stages, and the different monitoring manners.

6. The livestock and poultry body temperature monitoring system of claim 1, wherein the local server is further configured to:

compare with the normal body temperature change zone, a preprocessed body temperature value collected in real time for a target livestock and poultry individual selected from the plurality of livestock and poultry individuals in a target breeding region block of the plurality of breeding region blocks, and determine whether the preprocessed body temperature value falls within the normal body temperature change zone;

when the preprocessed body temperature value falls within the normal body temperature change zone, determine that a body temperature state of the target livestock and poultry individual is not abnormal and when the preprocessed body temperature value does not fall within the normal body temperature change zone, calculate, for each of (i) a first group comprising all of the plurality of livestock and poultry individuals in the target breeding region block and (ii) a second group comprising all of the livestock and poultry individuals in all of the plurality of breeding region blocks, a corresponding range [μ−3σ, μ+3σ] according to the following formulas:

$$\mu = \frac{\sum_{i=1}^{n} T_{cci}}{n}$$

$$\sigma = \sqrt{\frac{\sum_{i=1}^{n} (T_{cci} - \mu)^2}{n-1}}$$

wherein, for each of the first group and the second group, μ an average value of the preprocessed body temperature values in the corresponding group, σ is a standard deviation of the preprocessed body temperature values in the corresponding group-temperature, $T_{cci}$ represents an i-th preprocessed body temperature value in the corresponding group, and n is the number of livestock and poultry individuals in the corresponding group;

when the preprocessed body temperature value does not fall within the normal body temperature change zone, compare the preprocessed body temperature value with the corresponding range calculated for each of the first group and the second group;

for each comparison, when the preprocessed body temperature value is within the corresponding range, determine that the body temperature state of the target livestock and poultry individual is not abnormal;

for each comparison, when the preprocessed body temperature value is outside the corresponding range, determine that the body temperature state of the target livestock and poultry individual is abnormal; and when the body temperature state of the target livestock and poultry individual is determined to be abnormal, select the target livestock and poultry individual for rechecking, cause the infrared camera to move to the target breeding region block, recheck the target livestock and poultry individual, and further monitor the abnormal temperature state of the target livestock and poultry individual.

* * * * *